United States Patent
Hwang et al.

(10) Patent No.: US 9,861,301 B2
(45) Date of Patent: Jan. 9, 2018

(54) SERVICE METHOD AND SYSTEM FOR PROVIDING SERVICE USING MOVING PATH OF USER

(71) Applicant: NHN Entertainment Corporation, Seongnam-si (KR)

(72) Inventors: Gwang-Yeon Hwang, Seongnam-si (KR); Dae Woo Cho, Seongnam-si (KR); Jeong Kwon Yang, Seongnam-si (KR); Chung Hyun Yu, Seongnam-si (KR); Hye Ran Lee, Seongnam-si (KR); Kwang Min Kim, Seongnam-si (KR)

(73) Assignee: NHN Entertainment Corporation, Seongnam-si (KR)

( * ) Notice: Subject to any disclaimer, the term of this patent is extended or adjusted under 35 U.S.C. 154(b) by 215 days.

(21) Appl. No.: 14/487,571

(22) Filed: Sep. 16, 2014

(65) Prior Publication Data
US 2015/0081060 A1    Mar. 19, 2015

(30) Foreign Application Priority Data

Sep. 16, 2013 (KR) .................... 10-2013-0111239

(51) Int. Cl.
*A63F 9/24* (2006.01)
*A61B 5/11* (2006.01)
(Continued)

(52) U.S. Cl.
CPC ........... *A61B 5/1112* (2013.01); *A61B 5/1118* (2013.01); *G06F 19/30* (2013.01);
(Continued)

(58) Field of Classification Search
CPC ..... A63B 24/00; A63B 24/00; A63B 24/0062; A63B 71/06; A63B 5/1112; G01C 22/006
See application file for complete search history.

(56) References Cited

U.S. PATENT DOCUMENTS

| 6,463,385 | B1 * | 10/2002 | Fry | ........... A63B 24/0021 340/427 |
| 7,534,206 | B1 * | 5/2009 | Lovitt | ........... A61B 5/02438 482/8 |
| 2010/0323716 | A1 * | 12/2010 | Jaffri | ........... G06Q 30/02 455/456.1 |

(Continued)

FOREIGN PATENT DOCUMENTS

| JP | 2003316905 | 11/2003 |
| JP | 2003316905-050922 | 9/2005 |

(Continued)

OTHER PUBLICATIONS

Yuki Kuwano et al., "Development of Exercise Continuity Support System Using Location Information and Heart Rate", 2013 information Processing Society of Japan, vol. 3, No. 1, Mar. 2013, pp. 1-9.

(Continued)

*Primary Examiner* — Steve Rowland
(74) *Attorney, Agent, or Firm* — H.C. Park & Associates, PLC

(57) ABSTRACT

Disclosed is a service method and system for providing a service based on a moving path of a user. A service method configured as a computer may include receiving location information from a terminal of a user in response to a determination that a mode set by the user is an exercise mode, measuring a moving path of the user based on the location information, managing target information corresponding to at least one of a type of exercise that the user is doing and a predetermined path, and providing the target information to the user based on the measured moving path.

19 Claims, 18 Drawing Sheets

(51) Int. Cl.
*G06Q 10/06* (2012.01)
*G06Q 50/22* (2012.01)
*G06F 19/00* (2011.01)
*A61B 5/00* (2006.01)

(52) U.S. Cl.
CPC ..... *G06F 19/3481* (2013.01); *G06Q 10/0639* (2013.01); *G06Q 50/22* (2013.01); *A61B 5/0022* (2013.01); *A61B 5/6898* (2013.01); *A61B 5/7435* (2013.01); *A61B 2562/0219* (2013.01)

(56) References Cited

U.S. PATENT DOCUMENTS

| | | |
|---|---|---|
| 2012/0041767 A1 | 2/2012 | Hoffman et al. |
| 2012/0083705 A1* | 4/2012 | Yuen .................... A61B 5/0002 600/508 |
| 2012/0116550 A1* | 5/2012 | Hoffman ............ A63B 24/0084 700/91 |
| 2014/0164611 A1* | 6/2014 | Molettiere ........... A61B 5/6838 709/224 |
| 2014/0278220 A1* | 9/2014 | Yuen ....................... G01B 21/16 702/150 |
| 2015/0018991 A1* | 1/2015 | Arnold .............. G09B 19/0092 700/91 |
| 2015/0338236 A1 | 11/2015 | Hoffman et al. |

FOREIGN PATENT DOCUMENTS

| | | |
|---|---|---|
| JP | 2006072457 | 3/2006 |
| JP | 2008-304299 | 12/2008 |
| JP | 2010182230 | 8/2010 |
| JP | 2012-524638 | 10/2012 |
| JP | 2013037543 | 2/2013 |
| JP | 2013-536507 | 9/2013 |
| KR | 10-2003-0068788 | 8/2003 |
| KR | 10-2009-0132019 | 12/2009 |
| KR | 10-2012-0012187 | 2/2012 |
| WO | 2012021633 | 2/2012 |

OTHER PUBLICATIONS

Non-Final Office Action dated Aug. 3, 2016, in U.S. Appl. No. 14/487,453.
Non-Final Office Action ("Letter restarting period for response") dated Aug. 9, 2016, in U.S. Appl. No. 14/487,453.
Final Office Action dated Jan. 13, 2017, issued in U.S. Appl. No. 14/487,453.
Non-Final Office Action dated May 10, 2017, in U.S. Appl. No. 14/487,453.
Final Office Action dated Oct. 11, 2017, in U.S. Appl. No. 14/487,453.

* cited by examiner

SERVICE METHOD AND SYSTEM FOR PROVIDING SERVICE USING MOVING PATH OF USER

CROSS-REFERENCE TO RELATED APPLICATION

This application claims priority from and the benefit of Korean Patent Application No. 10-2013-0111239, filed on Sep. 16, 2013, which is hereby incorporated by reference for all purposes as if fully set forth herein.

BACKGROUND

Field

The present disclosure relates to a service method and system for providing a service based on a moving path of a user.

Discussion of the Background

A location based service system refers to a service system that may provide a variety of services to a user based on location information acquired through a location tracking system, such as a mobile communication network or a global positioning system (GPS).

Conventional location based services may provide a simple navigation service for climbing or cycling, may provide information about an exercise amount recorded, or may simply provide a record about a moving path of a user. The location based services have constraints in providing a service using only a current location of a user and accordingly, information about many activities of the user may not be utilized.

SUMMARY

Example embodiments provide a service method and system that may maintain and motivate an activity of a user by measuring and recording an activity of the user including a moving path and an exercise amount as well as a location of the user, by determining a ranking of the user based on the activity of the user, and by issuing digital content as a reward for the activity of the user.

Additional features of the invention will be set forth in the description which follows, and in part will be apparent from the description, or may be learned by practice of the invention.

Exemplary embodiments disclose a service method performed by a computer, the method including receiving location information from a terminal of a user in response to a determination that a mode set by the user is an exercise mode, measuring a moving path of the user based on the location information, managing target information corresponding to at least one of a type of exercise that the user is engaged in and a predetermined path, and providing, by the computer, the target information to the user based on the measured moving path.

Exemplary embodiments disclose a non-transitory computer-readable medium storing a program, when executed by a computer, to perform processing location information received from a terminal of a user in response to a determination that a mode set by the user is an exercise mode, measuring a moving path of the user based on the location information, managing target information corresponding to at least one of a type of exercise that the user is engaged in and a predetermined path, and providing, by the computer, the target information to the user based on the measured moving path.

Exemplary embodiments disclose a service system, including at least one memory, and at least one processor. The at least one processor may be configured to process a process of receiving location information from a terminal of a user in response to a determination that a mode set by the user is an exercise mode, a process of measuring a moving path of the user based on the location information, a process of managing target information corresponding to at least one of a type of exercise that the user is engaged in and a predetermined path, and a process of providing the target information to the user based on the measured moving path.

Exemplary embodiments disclose a file distribution system for distributing a file to install an application in a terminal of a user, the file distribution system including a file storage configured to store and maintain the file, and a file transmitter configured to transmit the file to the terminal in response to a request of the user. The application may include tone or more modules to control the terminal to display a user interface for selecting one of a daily mode and an exercise mode on a screen, to control the terminal to transmit location information to a service server in response to a selection on the exercise mode, to control the terminal to measure an exercise amount and to transmit the measured exercise amount to the service server in response to a selection on the daily mode, and to control the terminal to receive target information from the service server and to display the target information about the screen. The target information may correspond to at least one of a type of exercise that the user is engaged in and a predetermined path, and may be selected based on a moving path that is measured based on the location information.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention, and together with the description serve to explain the principles of the invention.

DETAILED DESCRIPTION OF THE ILLUSTRATED EMBODIMENTS

Figure 1:
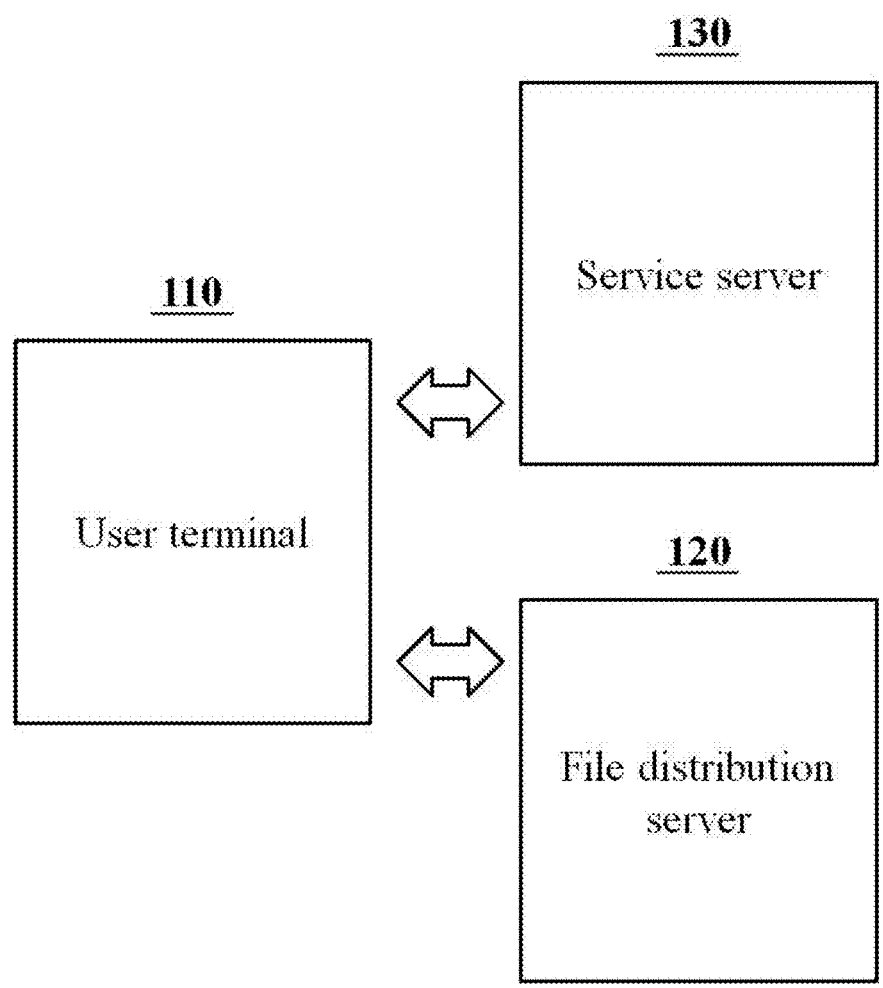
FIG. 1 illustrates an example of a service providing environment according to an exemplary embodiment of the present invention.

Exemplary embodiments of the present invention will be described in detail with reference to the accompanying drawings. These embodiments will be described in detail for those skilled in the art in order to practice the present invention. It should be appreciated that various illustrated embodiments of the present invention may be different from each other but do not have to be mutually exclusive. For example, specific shapes, configurations, and characteristics described in an exemplary embodiment of the present invention may be implemented in another embodiment without departing from the spirit and the scope of the present invention. In addition, it should be understood that position and arrangement of individual components in each disclosed embodiment may be changed without departing from the spirit and the scope of the present invention. Therefore, a detailed description described below should not be construed as being restrictive. In addition, the scope of the present invention is defined only by the accompanying claims and their equivalents if appropriate.

Similar reference numerals will be used to describe the same or similar functions throughout the accompanying drawings. It will be understood that for the purposes of this disclosure, "at least one of X, Y, and Z" can be construed as X only, Y only, Z only, or any combination of two or more items X, Y, and Z (e.g., XYZ, XYY, YZ, ZZ).

The terminology used herein is for the purpose of describing exemplary embodiments only and is not intended to be limiting of the invention. As used herein, the singular forms "a", "an", and "the" are intended to include the plural forms as well, unless the context clearly indicates otherwise. It will be further understood that the terms "comprises" and/or "comprising", when used in this specification, specify the presence of stated features, integers, steps, operations, elements and/or components, but do not preclude the presence or addition of one or more other features, integers, steps, operations, elements, components, and/or groups thereof.

It will be understood that when an element is referred to as being "connected to" another element, it can be directly connected to the other element, or intervening elements may be present.

Hereinafter, exemplary embodiments of the present invention are described in detail with reference to the accompanying drawings.

FIG. 1 illustrates an example of a service providing environment according to an exemplary embodiment of the present invention. FIG. 1 illustrates a user terminal 110, a file distribution server 120, and a service server 130.

The user terminal 110 may include a mobile terminal of a user, for example, a smartphone, a personal digital assistant (PDA), a tablet computer, a smart watch, an electronic glass (e.g., Google Glass™), and the like. An application for being provided with a service according to embodiments of the present invention may be installed in the user terminal 110. For example, the user terminal 110 may use a service provided from the service server 130 through a communication with the service server 130 according to a control of the application.

The file distribution server 120 may include a server configured to distribute a file for installing an application. For example, the file distribution server 120 may store and manage the file, and may provide the stored file to the user terminal 110 in response to a request of the user terminal 110. Here, the user terminal 110 may install the application using the file provided from the file distribution server 120, and may be provided with an associated service using the installed application. The file distribution server 120 may be a server included in the service server 130, or may be a server associated with the service server 130 as a server of a third party.

The service server 130 may be a server for providing a service according to embodiments of the present invention, and may provide the service by transmitting and receiving data to and from the user terminal 110 in which the application is installed. The service may include a service for recording daily life of the user, a service for supporting activities of the user, and a service for providing a digital space in which users may sympathize with mutual activities.

According to aspects, the service server 130 may measure and record an activity of the user based on information received from the user terminal 110. Here, the activity of the user may be measured based on a moving path and an exercise amount of the user. The moving path may be measured and recorded based on location information of the user terminal 110. For example, the application installed in the user terminal 110 may control the user terminal 110 to transmit global positioning system (GPS) information to the service server 130 based on a predetermined condition, e.g., when a service application for recognizing the location of the user terminal 110 is executed. The service server 130 may measure and record the moving path of the user based on the GPS information received from the user terminal 110. Further, the moving path of the user may be determined in the user terminal 110. Also, the exercise amount may be measured and recorded based on at least one of calories, a moving distance, a moving time, a moving speed, a moving pace, and an altitude. Activities of the user may be classified into daily life and exercise. According to a configuration, a progress of a mini game and the like may be selectively added as the activity of the user.

The exercise may indicate an activity of a user to measure at least one of a location of the user, a moving path of the user, and an exercise amount of the user based on a predetermined type of exercise selected by the user, for example, stepping, walking, running, cycling, and climbing. Here, in the case of exercise, a variety of information, such as calories, a moving distance, a moving time, a moving speed, and an altitude, may be measured and recorded based on location information, for example, GPS information received from the user terminal 110 and/or other sensed information sensed by one or more sensors including an accelerometer, a proximity sensor, a gyroscope, a moisture sensor, and the like. The daily life may indicate an activity of a user to measure a daily exercise amount of the user using, for example, a gravity sensor and an acceleration sensor. Here, location information of the user terminal 110 may not be used, or may be selectively used.

Also, the service server 130 may determine rankings of users based on activities of the users, and may maintain and motivate an activity of a user by issuing and providing digital content to the user as a reward for the activity. For example, during the activity of the user, digital content may be provided to the user based on an activity record of the user, such as reaching a predetermined location, moving along a predetermined moving path, or achieving a predetermined exercise amount. The user terminal 110 may communicate with an exercise machine, such as a treadmill, to receive exercise data. Also, when the activity of the user ends, digital content may be further provided based on an activity amount of the user. The digital content may be provided in a form of, for example, a badge, a digital coupon, and points. The digital content may be saved in a personal profile area and may be converted to digital currency that can be used at a designated online or offline store. Although digital contents were described in terms of rewards, aspects of the invention are not limited thereto, such that penalties may also be issued to encourage users to perform activities.

The service server 130 may provide a service that enables users to share records and/or that enables users doing similar activities to be connected to each other. For example, rankings may be provided to users based on an exercise amount, an activity amount, or points. A user may challenge a record achieved by another user who is ranked higher than the user.

Further, the service server 130 may manage a challenge created by a predetermined user or an affiliated company. The challenge may include a multi-user exercise, for example, a marathon and a cycling game, which requires participation of multiple users. For example, the affiliated company may create a challenge by holding a marathon game. Users may participate into the challenge by using digital content or digital currency as an application fee, and may acquire an additional reward, for example, digital content or digital currency based on a result of participating in the challenge.

As described above, digital content such as a badge or a coupon may be provided to the user based on an exercise amount of the user, GPS information, and a moving path. Digital content such as points in a virtual game, may be provided to the user based on an activity amount (e.g., number of steps walked or distance traveled) of the user. Also, additional digital content such as a badge, a coupon, or points may be further provided to the user through other activities other than daily life and exercise of the user. The other activities may include "making a friend", activity related posting such as a photo and an opinion, a comment activity about a posting of a friend, and playing a mini game.

Figure 2:
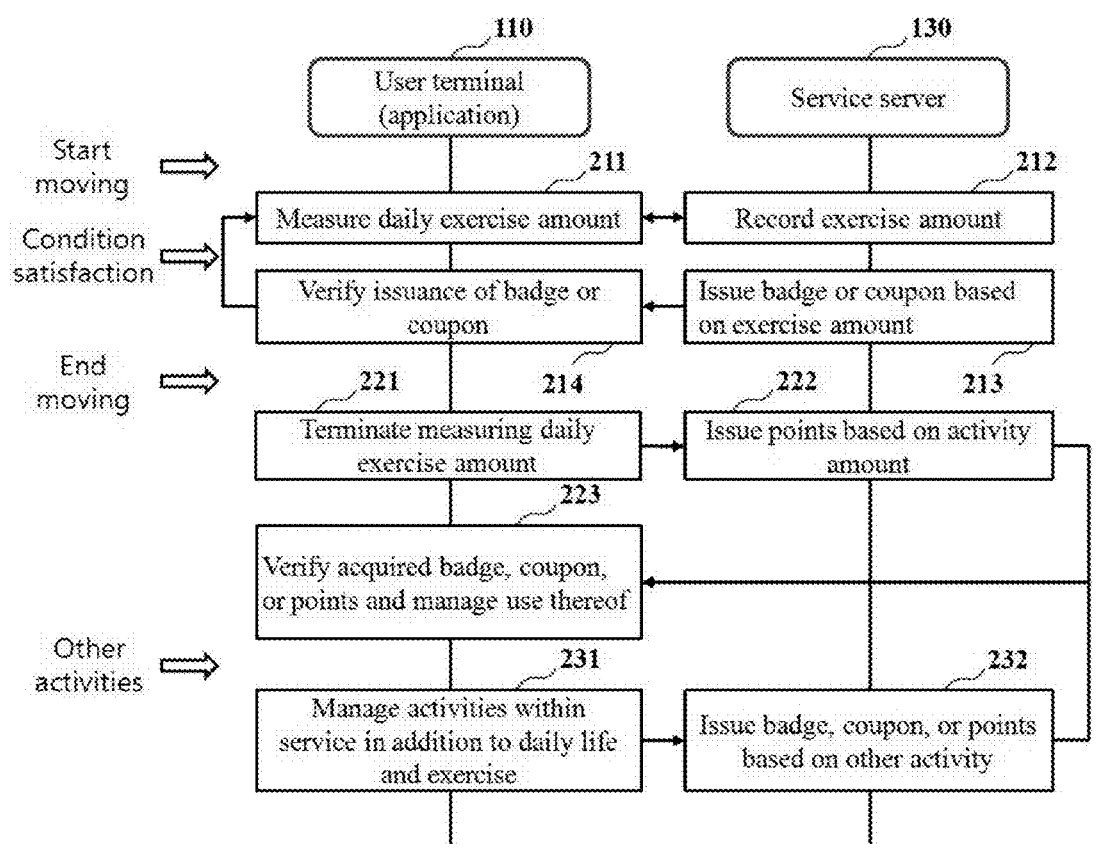
FIG. 2 is a flowchart illustrating an example of a process of issuing digital content based on daily life in an activity of a user according to an exemplary embodiment of the present invention.

FIG. 2 is a flowchart illustrating an example of a process of issuing digital content based on daily life in an activity of a user according to an exemplary embodiment of the present invention. A user may select one of "daily life" and "exercise", which are classified as different activities of a user, using a user interface of an application. As described above, "daily life" may indicate an activity of the user to measure a daily exercise amount of the user using, for example, a gravity sensor and an acceleration sensor.

The user may select "daily life" and then may start moving. In response thereto, the user terminal 110 and the service server 130 may perform the following operations. Here, the user terminal 110 may perform the following operations according to a control of an application. However, aspects are not limited to the following operations.

In operation 211, the user terminal 110 may measure a daily exercise amount. For example, "daily life" may include a pedometer function. In this case, the user terminal 110 may measure step counts of the user as an exercise amount using one or more sensors for the pedometer function, for example, a gravity sensor and an acceleration sensor. The measured exercise amount may be transmitted to the service server 130.

In operation 212, the service server 130 may record the exercise amount.

Here, operations 211 and 212 may be repeatedly performed while "daily life" selected by the user continues. For example, the user terminal 110 may transfer the measured exercise amount to the service server 130 at predetermined intervals and the service server 130 may continuously or periodically record the received exercise amount.

Further, in addition to the recording of the exercise amount, the service server 130 may verify whether the exercise amount of the user has satisfied a predetermined condition. The verification process may be performed substantially simultaneously when the exercise amount is recorded. If the predetermined condition is satisfied, operations 213 and 214 may be performed.

In operation 213, the service server 130 may issue a badge or a coupon based on the exercise amount. For example, if the predetermined condition is satisfied when the user walks a certain number of steps, e.g., 10,000 steps in an example of a pedometer function, and if an exercise amount corresponding to 10,000 steps is recorded, the service server 130 may issue a badge or a coupon to the user as predetermined digital content based on the corresponding exercise amount. Here, the service server 130 may transmit, to the user terminal 110, a notification message about the issuance of the digital content.

In operation 214, the user terminal 110 may verify the issuance of the badge or the coupon. For example, in response to the notification message received from the service server 130, the user terminal 110 may inform the user that the badge or the coupon is issued to the user.

Operation 211 may be performed again after the completion of the operation 214 and thus, the user terminal 110 may continuously measure the daily exercise amount and the service server 130 may monitor the exercise amount of the user after a predetermined condition is satisfied.

When the user stops moving, operations 221 through 213 may be performed. The termination of the user's moving may be automatically detected at the user terminal 110 and/or may be detected through a signal input from the user.

In operation 221, the user terminal 110 may terminate measuring the daily exercise amount. Here, the user terminal 110 may indicate the service server 130 about the termination in measuring the daily exercise amount.

In operation 222, the service server 130 may issue points based on an activity amount. For example, the service server 130 may measure the overall activity amount according to a progress of "daily life", may calculate points corresponding to the measured activity amount, and may issue the calculated points to the user.

In operation 223, the user terminal 110 may verify the acquired badge, coupon, or points, and may manage the use thereof. For example, the user terminal 110 may display information about the acquired badge, coupon, or points on a screen, so that the user may verify acquired digital content, and may provide a predetermined user interface so that the user may use the acquired digital content. For example, the user may convert the acquired digital content to digital currency that can be used at a store, and may purchase another digital content using the digital currency.

Also, as described above, the digital content may also be acquired through another activity, for example, "making a friend", activity related posting such as a photo and an opinion, a comment activity about a posting of a friend, and playing a mini game. When the other activity is performed, operations 231 and 232 may be performed.

In operation 231, the user terminal 110 may manage activities within the range of a service in addition to "daily life" and "exercise". In this case, the user terminal 110 may provide a service so that the user may perform another activity according to a control of the application.

In operation 232, the service server 130 may issue a badge, a coupon, or points based on the other activity. After operation 232, the user terminal 110 may perform operation 223 again.

Figure 3:
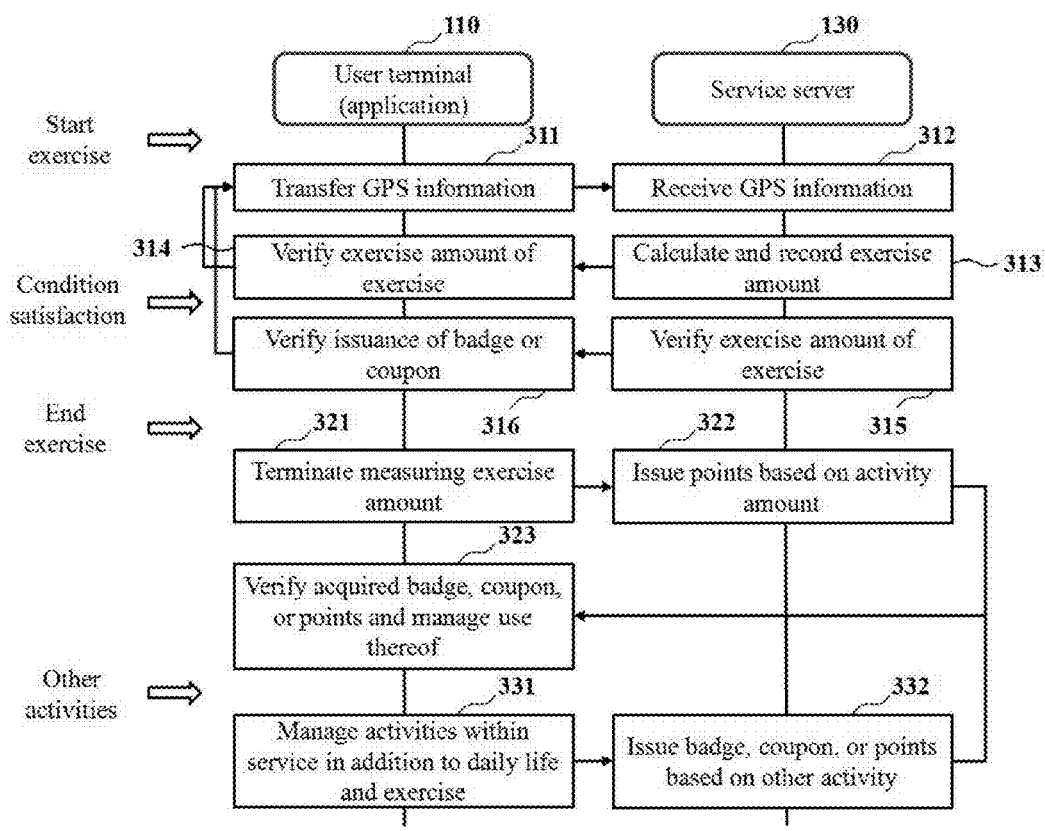
FIG. 3 is a flowchart illustrating an example of a process of issuing digital content based on exercise in an activity of a user according to an exemplary embodiment of the present invention.

FIG. 3 is a flowchart illustrating an example of a process of issuing digital content based on exercise in an activity of a user according to an exemplary embodiment of the present invention. A user may select one of "daily life" and "exercise", which are classified as different user activities, using a user interface of an application. As described above, "exercise" may indicate an activity of the user to measure at least one of a location of the user, a moving path of the user, and an exercise amount of the user based on a predetermined type of exercise selected by the user, for example, stepping, walking, running, cycling, and climbing.

The user may select a type of "exercise" and then may start the selected exercise. In response thereto, the user terminal 110 and the service server 130 may perform the following operations. Here, the user terminal 110 may perform the following operations according to a control of an application. However, aspects are not limited as such.

In operation 311, the user terminal 110 may transfer GPS information. For example, the user terminal 110 may create location information and may transmit the location information to the service server 130.

In operation 312, the service server 130 may receive the GPS information. For example, the service server 130 may receive and manage location information transmitted from the user terminal 110.

In operation 313, the service server 130 may calculate and record an exercise amount. Here, the exercise amount may be calculated based on a change in location information of the user terminal 110 according to a type of exercise.

In operation 314, the user terminal 110 may verify the exercise amount of the exercise. For example, the service server 130 may transfer the calculated exercise amount to the user terminal 110, and the user terminal 110 may verify the transferred exercise amount and display the verified exercise amount on a screen.

Here, operations 311 through 314 may be repeatedly performed while the exercise continues. Accordingly, the service server 130 may monitor a location of the user, an exercise amount, or a moving path.

If a predetermined condition is satisfied, the service server 130 may perform the following operations.

In operation 315, the service server 130 may issue a badge or a coupon based on the location or the exercise amount of the user.

In operation 316, the user terminal 110 may verify the issuance of the badge or the coupon.

Here, operation 311 may be performed again whereby the location and the exercise amount about the exercise may be continuously measured.

When the user finishes exercise, operations 321 through 323 may be performed. The termination of the exercise of the user may be automatically detected at the user terminal 110 and/or may also be detected through a signal input from the user.

In operation 321, the user terminal 110 may terminate measuring the exercise amount. Here, the user terminal 110 may indicate the service server 130 about the termination in measuring the exercise amount.

In operation 322, the service server 130 may issue points based on an activity amount. For example, the service server 130 may measure the overall activity amount according to a progress of "exercise", for example, an activity amount according to a movement and an activity amount according to an exercise amount, may calculate points corresponding to the measured activity amount, and may issue the calculated points to the user.

In operation 323, the user terminal 110 may verify the acquired badge, coupon, or points, and may manage the use thereof. For example, the user terminal 110 may display information about the acquired badge, coupon, or points on a screen, so that the user may verify acquired digital content, and may provide a predetermined user interface so that the user may use the acquired digital content. For example, the user may convert the acquired digital content to digital currency at a store, and may purchase another digital content using the digital currency.

Further, as described above, the digital content may be acquired through another activity, for example, "making a friend", activity related posting such as a photo and an opinion, a comment activity about a posting of a friend, and playing a mini game. If the other activity is performed, operations 331 and 332 may be performed.

In operation 331, the user terminal 110 may manage activities within the range of a service in addition to "daily life" and "exercise". In this case, the user terminal 110 may provide a service so that the user may perform another activity according to a control of the application.

In operation 332, the service server 130 may issue a badge, a coupon, or points based on the other activity. After the operation 332, the user terminal 110 may perform operation 323 again.

Figure 4:
FIG. 4 illustrates an example of a screen for a user to select a type of exercise according to an exemplary embodiment of the present invention.

FIG. 4 illustrates an example of a screen 400 for a user to select a type of exercise according to an exemplary embodiment of the present invention. The screen 400 is an example of a screen of the user terminal 110. Referring to FIG. 4, a user interface that enables the user to select a type of exercise, for example, stepping, power walking, running, cycling, and climbing is displayed on the screen 400. In response to a selection of the user on a predetermined type of exercise using the user interface displayed on the screen 400, the process of FIG. 3 corresponding to the selected type of exercise may be performed.

According to another embodiment, when a user finishes exercise, rankings may be determined among users based on an exercise amount. Users may verify rankings for each detailed item. Also, the users may acquire additional digital content, for example, a badge, a coupon, and points, by challenging records of other users who are ranked higher than the user. In addition, rankings may be determined even for a mini game. Even with respect to the mini game, users may acquire additional digital content by challenging records of higher ranking users.

Figure 5:
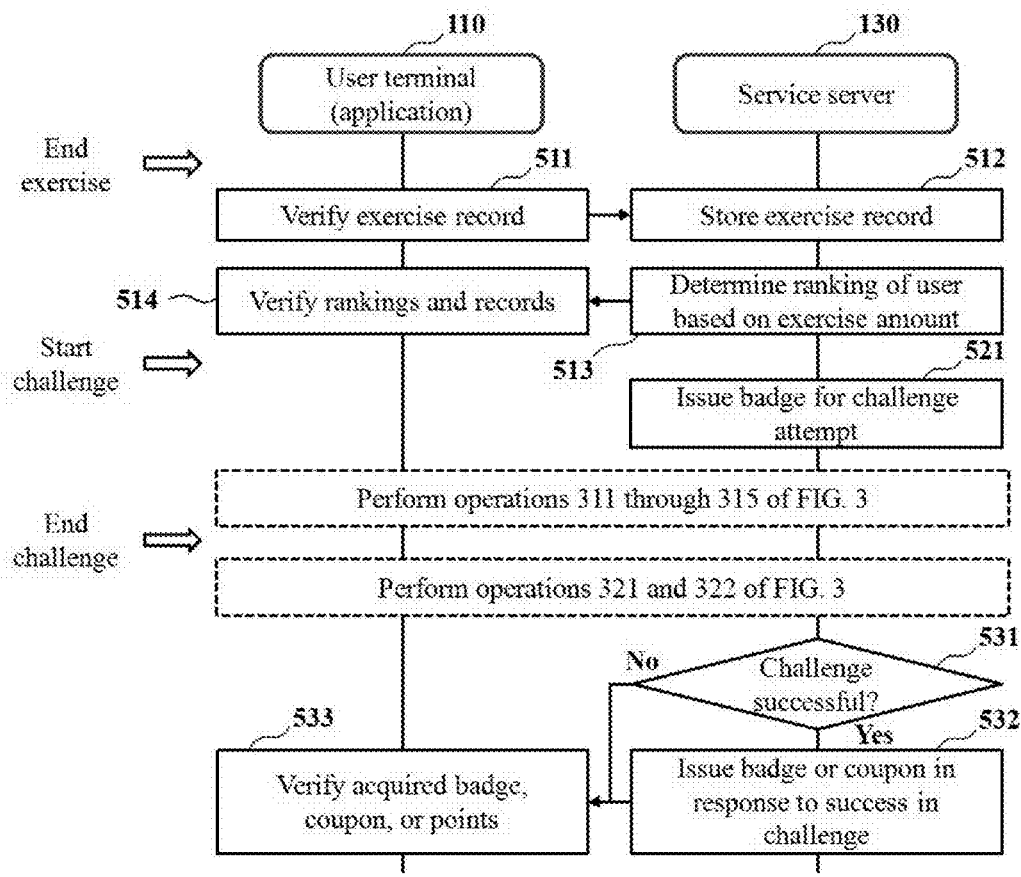
FIG. 5 is a flowchart illustrating an example of a process of determining a ranking and challenging a record according to an exemplary embodiment of the present invention.

FIG. 5 is a flowchart illustrating an example of a process of determining a ranking and challenging a record according to an exemplary embodiment of the present invention.

If a user finishes exercise, the following operations may be performed. However, aspects are not limited as such.

In operation 511, the user terminal 110 may verify an exercise record(e.g., a moving or traveled path) corresponding to the performed exercise activity. The exercise record may include a moving path of the user and an exercise amount. Here, the moving path of the user indicates a moving path of the user terminal 110.

In operation 512, the service server 130 may store the exercise record.

In operation 513, the service server 130 may determine a ranking of the user based on the exercise amount. In this instance, rankings of users may be determined for each detailed item, for example, overall rankings, rankings for each type of exercise, (e.g., calories, a moving speed, a moving time, and a moving distance), and rankings for each moving path. As described above, a type of exercise amount may include at least one of calories, a moving distance, a moving time, a moving speed, and an altitude.

In operation 514, the user terminal 110 may verify rankings and records.

Here, if the user starts challenging an exercise record of a friend who is ranked higher than the user, the following operations may be performed. The start of challenge may be recognized at the user terminal 110 in response to an input of the user through a user interface provided from the user terminal 110 according to a control of an application, and may be informed to the service server 130.

In operation 521, the service server 130 may issue a badge for the challenge attempt. Here, operation 521 relates to enhancing the user's interest in the challenge and thus, may be selectively performed. Accordingly, the operation 521 may be omitted in accordance with a configuration.

If the user starts exercise in response to the start of challenge, operations 311 through operation 315 of FIG. 3 may be performed. If the user finishes the challenge, for example, when the user finishes exercise, operations 321 and 322 of FIG. 3 may be performed.

In operation 531, the service server 130 may determine whether the challenge is successful. For example, if the user has passed the same path within a faster time than a selected friend, or if the user moves a further distance than the selected friend, the service server 130 may determine that the challenge of the user is successful. Information regarding whether the challenge is successful may be provided to the user through the user terminal 110.

In operation 532, the service server 130 may issue a badge or a coupon in response to the success in the challenge.

In operation 533, the user terminal 110 may verify the acquired badge, coupon, or points.

According to exemplary embodiments, predetermined digital content such as a badge or a coupon may be collected and edited through an item book. Also, the user may additionally acquire digital contents desired to be added through challenging. For example, if an exercise record is present for each badge and the user achieves the corresponding exercise record through challenging, the corresponding badge may be provided to the user. As an example, if a predetermined badge is provided in response to completing the full B course of mountain A, the user may acquire the corresponding badge by challenging and completing the full B course of mountain A. Such badges may be produced and serviced in various forms, such as 10 km walking and completing a predetermined course.

Figure 6:
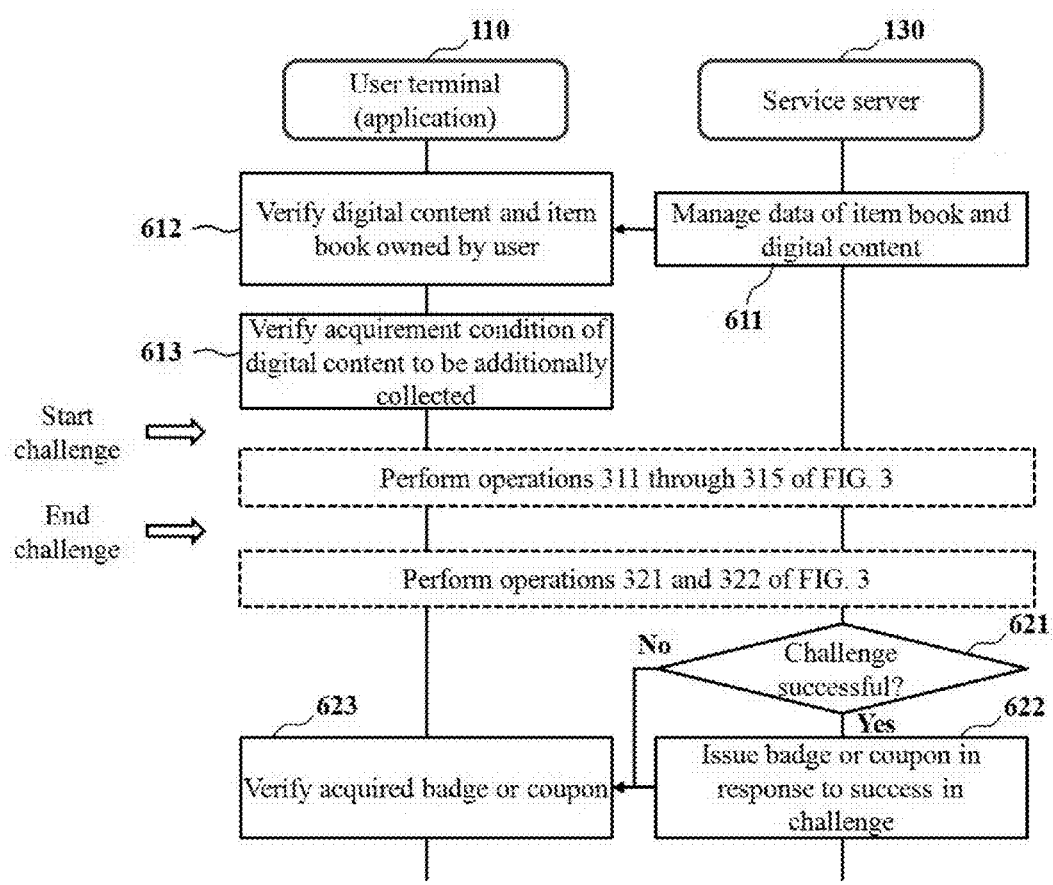
FIG. 6 is a flowchart illustrating an example of a process of challenging and collecting a badge according to an exemplary embodiment of the present invention.

FIG. 6 is a flowchart illustrating an example of a process of challenging and collecting a badge according to an exemplary embodiment of the present invention.

In operation 611, the service server 130 may manage data of an item book and digital content. Such data may be provided to the user terminal 110 in response to a request of the user terminal 110.

In operation 612, the user terminal 110 may verify the digital content and the item book owned by a user.

In operation 613, the user terminal 110 may verify an acquirement condition of digital content to be additionally collected.

If the user selects digital content to be additionally collected and starts challenge, operations 311 through 315 of FIG. 3 may be performed. If the user finishes the challenge, for example, when the user finishes exercise, operations 321 and 322 of FIG. 3 may be performed.

In operation 621, the service server 130 may determine whether the challenge is successful. For example, if the user achieves an exercise record corresponding to an acquirement condition, the service server 130 may determine that the challenge of the user is successful.

Information regarding whether the challenge is successful may be provided to the user through the user terminal 110.

In operation 622, the service server 130 may issue a badge or a coupon in response to the success in the challenge.

In operation 623, the user terminal 110 may verify the acquired badge, coupon, or points.

According to exemplary embodiments, points of digital content may be converted to digital currency available at a store associated with the service server 130. The digital currency may be defined as "energy", and the digital currency may be acquired by converting the points, or may be purchased. Here, the energy may not be converted to points. The user may purchase, at the store with the energy, for example, a badge, an item book, a giftcon capable of being inserted into the badge for editing the badge, and a mini game. Also, a predetermined badge may be sold. In this case, points acquired by selling the predetermined badge may be converted to energy and thereby be used to purchase another digital content.

According to exemplary embodiments, a basic item book may be issued together with the issuance of a badge. Badges in an item book category may be automatically moved to a corresponding item book. The user may edit, for example, add, move, and delete, and thereby collect badges from the item book. Also, an additional badge and item book may be purchased at a store with energy and thereby added. An item book available through a direct configuration and edition of the user may be provided. If the user owns a duplicate badge or a badge owned by the user becomes unnecessary, the user may exchange the corresponding badge with another user or may exchange the corresponding badge with energy.

According to exemplary embodiments, digital content may further include a message item. The message item may include an item that allows the user to assign a message for a predetermined user at a predetermined location, section, or path. For example, a user A may assign a message "I love you" for a user C at a section B. In this example, when the user C passes the section B, the message "I love you" may be provided to a user terminal of the user C. Further, an advertiser may assign an advertisement message for all the users at a predetermined location. Also, a message may include digital content, for example, a badge, a coupon, and points. For example, an advertisement message and a coupon may be provided to a corresponding user. In the above example, the user A may provide, to the user C, the message "I love you" and predetermined points as gifts. That is, a message may be provided in a form of "phrase" or "phrase+reward". The reward may be provided in a form of digital content or a coupon that is downloaded from the user terminal and thereby immediately available for the recipient. Also, a message item may be used when the user provides a message and a reward to him/herself.

According to exemplary embodiments, the service method may include providing a reward for an activity of a user based on a moving path of the user, for example, a map path of a corresponding section, a moving distance, and an exercise record, instead of using a predetermined location. For example, the service method may provide information or associate an advertisement or an event by targeting users that pass a predetermined map path, for example, a bicycle road and a marathon course.

Also, friends or users may exercise together by setting a goal of a predetermined map path or distance path and by challenging other users. Challenging between users may be induced by providing digital content, for example, a badge that may be acquired based on the predetermined map path, moving distance, and exercise record such as a time and a speed. For example, additional digital content including digital reward items, such as a badge, points, or a coupon, may be provided as a reward for an activity of the user based on a moving path of the user, such as an amount of time used to pass a predetermined path or a distance used to pass the predetermined moving path.

Also, a ranking of the user may be determined based on an exercise record for each moving path of the user. The exercise record may be shared between users. A challenging service for the exercise record may be provided.

Figure 7:
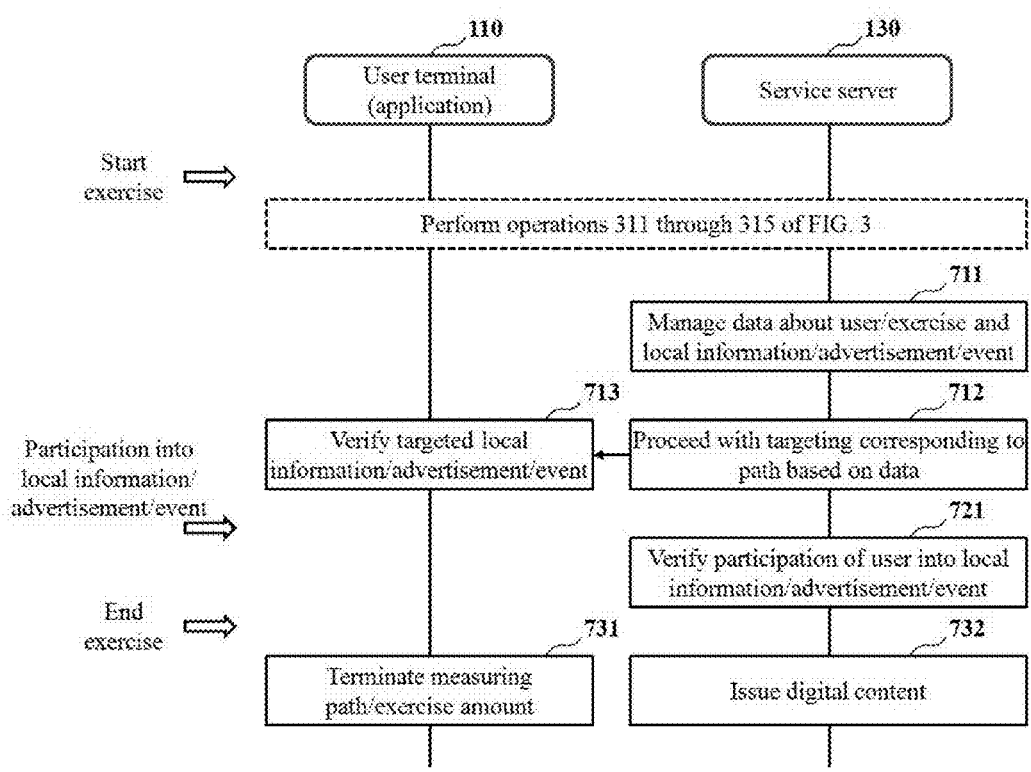
FIG. 7 is a flowchart illustrating an example of a process of issuing digital content and providing target information based on a path according to an exemplary embodiment of the present invention.

FIG. 7 is a flowchart illustrating an example of a process of issuing digital content and providing target information based on a path according to an exemplary embodiment of the present invention.

When a user starts excise, operations 311 through 315 of FIG. 3 may be performed.

In operation 711, the service server 130 may manage data about the user, the exercise, and target information, for example, local information, an advertisement, and an event. For example, the service server 130 may verify a type of exercise that the user is engaged in, for each user, and may verify a moving path and an exercise amount of the user through operations 311 through 315. Further, the service server 130 may verify local information for each area or information about an advertisement or an event.

In operation 712, the service server 130 may perform targeting corresponding to a path based on the data. More specifically, the service server 130 may obtain or determine target location information, advertisement, event or the like based on the path, exercise activity and/or or corresponding data. For example, the service server 130 may determine a target user associated with local information, the advertisement, or the event, based on the type of exercise that the user is engaged in. The local information, the advertisement, or the event to be provided to the user may be determined based on one or more parameters, such as the type of exercise, the exercise amount, the moving path, and the like.

In operation 713, the user terminal 110 may verify the targeted local information, advertisement, or event. For example, the user terminal 110 may receive, from the service server 130, the local information, the advertisement, or the event, and may display the same on a screen to provide the same to the user.

If the user utilizes, applies for, or participates into the local information, the advertisement, or the event, the following operation may be performed.

In operation 721, the service server 130 may verify the utilization, the application, or the participation of the user in the local information, the advertisement, or the event.

When the user finishes exercise, the following operations may be performed.

In operation 731, the user terminal 110 may terminate measuring a path and an exercise amount. Here, the user terminal 110 may inform the service server 130 about the termination in measuring the path and the exercise amount.

In operation 732, the service server 130 may issue digital content. Here, instead of simply providing only points according to an activity amount, the service server 130 may provide, to the user, at least one of digital content according to the path and predetermined digital content according to the utilization, the application, or the participation in the local information, the advertisement, or the event, and may selectively provide points according to the activity amount.

As described above, the user may challenge a badge, an event, or a challenge targeted at a predetermined map path and a distance path. A method of challenging a badge is described above with reference to FIG. 6. As described above, the challenge may include exercise, for example, a marathon and a cycling game that requires participation of multiple users. The map path may indicate a predetermined path on a map, and the distance path may indicate a path that satisfies a predetermined distance.

According to an exemplary embodiment, the service method may connect users not based on a predetermined location but based on a moving path of a user, and may induce relevant users to share information, e.g., user information, activity information, and purchase information, or to perform an activity, e.g., a friend recommendation, a challenge, an event, and a mini game, together. For example, the service method may inform users passing a predetermined path A of a user that has passed or is currently passing the predetermined path A, and may induce the users to share information and perform an activity together.

To this end, the service server 130 may collect data about moving paths that overlap by at least a predetermined numerical value, may group and connect users of a corresponding moving path, and may induce users within the same group to share information and perform an activity together.

For example, the service server 130 may track moving paths of a user A and a user B that are passing a predetermined path. In this example, when the user A and the user B have moved at least N % of the predetermined path, the service server 130 may connect the user A and the user B to a single group and may provide group information to each of the user A and the user B. Although grouping and connecting two users is described as an example, it is also possible to group and connect at least three users having moved at least N % of a predetermined path.

Here, a user included in a group may verify information about a badge, a ranking, a challenge, and a game of another user within the group, and may take an action such as adding the other user as a friend, inviting the other user to a mini game, challenging a record of the other user, or recommending or sharing a challenge to or with the other user. Here, the service server 130 may transfer a request for a corresponding action to the other user. In response thereto, the other user may take a response action, such as verifying or accepting a friend invitation, accepting a challenge recommendation, or accepting an invitation to the mini game. The service server 130 may process a process, such as a friend addition, a progress of a mini game, or a challenge sharing, by connecting the user and the other user in response to the response action.

According to an exemplary embodiment, the service method may attract a user by issuing digital content, e.g., a position of interest (POI) badge based on a predetermined "location" and "path" along a moving path during an activity of the user, and may induce the user to expand activity coverage of the user. For example, the service server 130 may calculate a location of the user using a Geo-Hash algorithm. The Geo-Hash algorithm refers to a latitude/longitude Geo-code system. The service server 130 may calculate the location of the user using rectangles defined as a 5-digit character string (error range±2.4 km) and a 7-digit character string (error range±76 m) by the Geo-Hash algorithm, for example.

Figure 8:
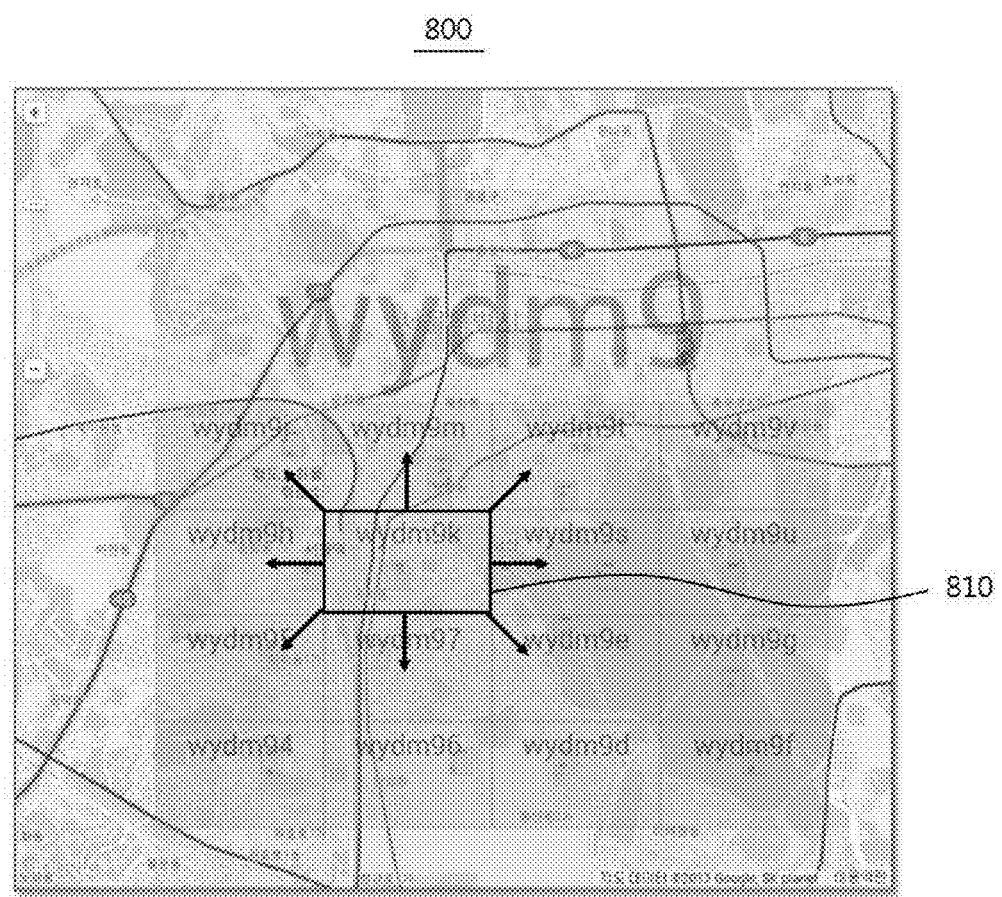
FIG. 8 illustrates an example of a change in a location of a user using a Geo-Hash algorithm according to an exemplary embodiment of the present invention.

FIG. 8 illustrates an example of a change in a location of a user using a Geo-Hash algorithm according to an exemplary embodiment of the present invention. Referring to FIG. 8, a single rectangle defined as a 5-digit character string "wydm9" and rectangles defined as a 6-digit character string are displayed on a map screen 800. The rectangles defined by 6-digit character strings may be included within the boundary of the single rectangle defined by 5-digit character string. When a rectangle 810, which may be defined by 6-digit character string, is assumed as a rectangle corresponding to GPS information of the user, a subsequent moving location of the user may have 8 bearings as indicated by arrow indicators on the map screen 800. Although rectangles having a string of certain number of characters are described above, aspects of the invention are not limited thereto, such that the different shapes and number of character strings may be used. Further, according to aspects of the invention, moving direction or location of the user may have less that or greater than 8 bearings as described above.

"Location" based digital content may be issued in real time. To this end, the service server 130 may calculate badges predictable to be issued, may store the calculated badges in the user terminal 110 through an application, and may issue and verify a corresponding badge immediately in response to a location movement of the user.

Figure 9:
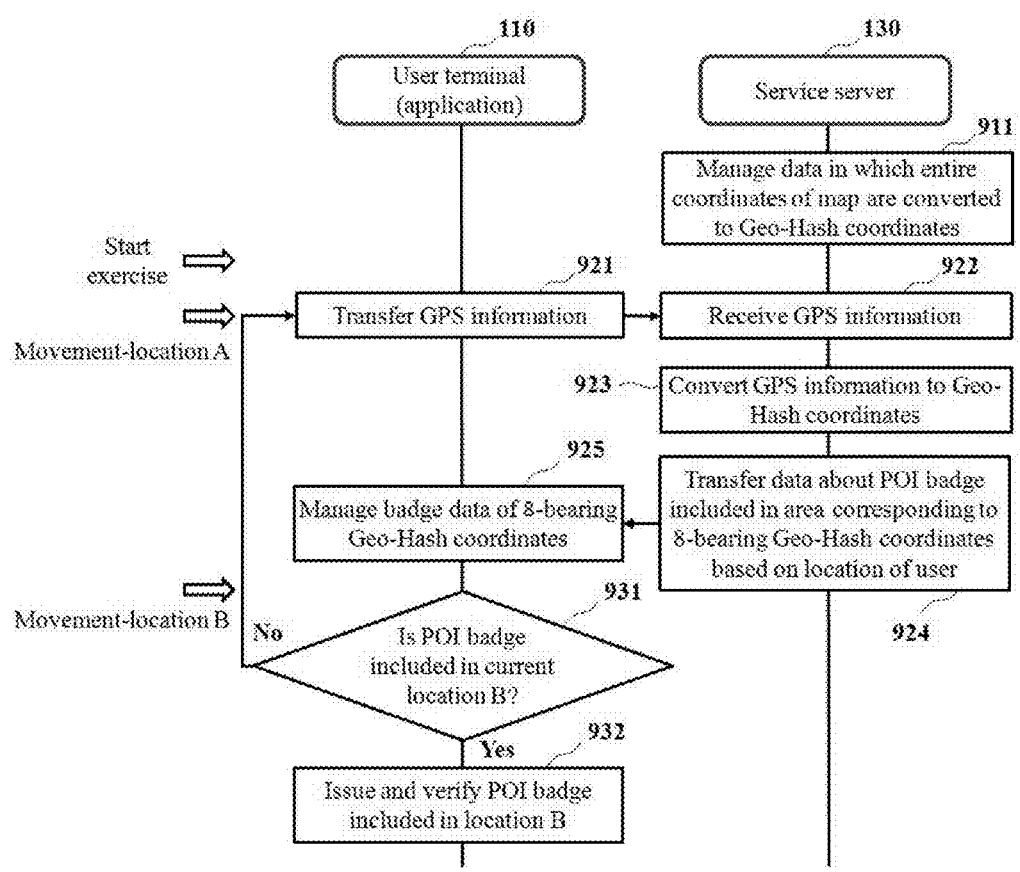
FIG. 9 is a flowchart illustrating an example of a process of issuing a location based position of interest (POI) badge according to an exemplary embodiment of the present invention.

FIG. 9 is a flowchart illustrating an example of a process of issuing a location based POI badge according to an exemplary embodiment of the present invention.

In operation 911, the service server 130 may manage data in which the entire coordinates of a map are converted to Geo-Hash coordinates.

If a user starts exercise, the following operations may be performed.

In operation 921, the user terminal 110 may transfer GPS information. For example, the user terminal 110 may transmit the GPS information to the service server 130.

In operation 922, the service server 130 may receive the GPS information.

In operation 923, the service server 130 may convert the GPS information to Geo-Hash coordinates. For example, the service server 130 may convert the GPS information to the Geo-Hash coordinates based on the data managed in the operation 911.

In operation 924, the service server 130 may transfer data about a POI badge included in an area corresponding to 8-bearing Geo-Hash coordinates, based on the location of the user. However, aspects of the invention are not limited thereto, such that other digital content may be issued based on POI. Further, the Geo-Hash coordinates may have less than or greater than 8-bearings. For example, as described above with reference to FIG. 8, movements of eight bearings may occur based on a single rectangle on the Geo-Hash coordinates. In response to the movements of eight bearings, the service server 130 may provide, to the user terminal 110 in advance, data about POI badges included in the corresponding area.

In operation 925, the user terminal 110 may manage badge data of 8-bearing Geo-Hash coordinates. As described above, "location" based digital content needs to be issued in real time and thus, the service server 130 may provide, to the user terminal 110 in advance, data about POI badges included in an area corresponding to 8-bearing Geo-Hash coordinates predictable as a next location, before the user moves.

If it is verified the user moved from a location A to a location B, the following operations may be performed.

In operation 931, the user terminal 110 may verify whether a POI badge is included in a current location, for example, the location B. If the POI badge is included in the current location B, the user terminal 110 may perform operation 932. Conversely, if the POI badge is not included in the current location B, the user terminal 110 may track a movement of the user by returning to the operation 921.

In operation 932, the user terminal 110 may issue and verify the POI badge included in the location B.

If the user finishes exercise, a measurement at the user terminal 110 may be terminated. Information about the badge acquired by the user terminal 110 may be transferred to the service server 130.

Further, in the case of "path" based digital content, data about a path or a path and a badge may be stored in the service server 130. The path and an issuable badge may be checked and issued at a time by transferring a moving path to the service server 130 at the end of the user movement round.

Figure 10:
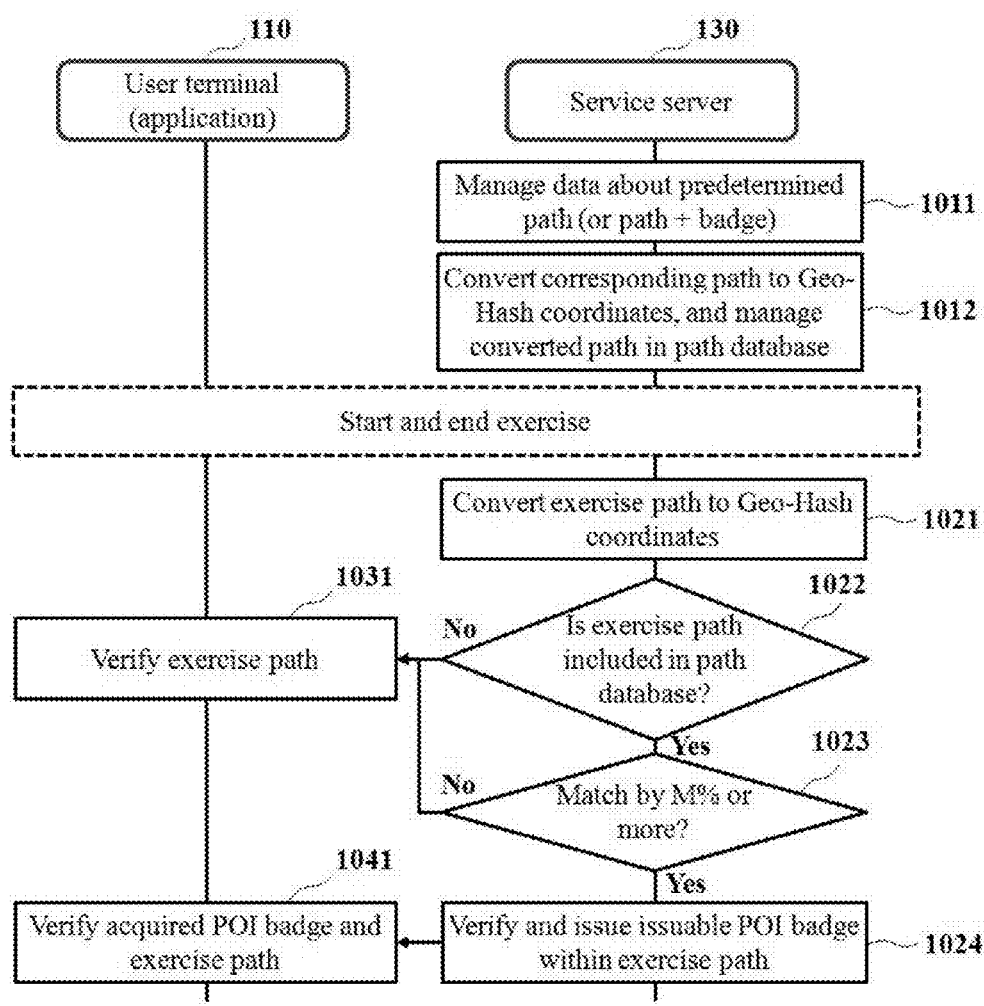
FIG. 10 is a flowchart illustrating an example of a process of issuing a path based POI badge according to an exemplary embodiment of the present invention.

FIG. 10 is a flowchart illustrating an example of a process of issuing a path based POI badge according to an exemplary embodiment of the present invention.

In operation 1011, the service server 130 may manage data about a predetermined path or data about a path and a badge. That is, in the case of a path in which digital content such as a badge is present, data about the digital content and the path may be associated with each other and thereby managed.

In operation 1012, the service server 130 may convert the corresponding path to Geo-Hash coordinates, and thereby manage the converted path in a path database.

If the user starts and finishes exercise, the following operations may be performed.

In operation 1021, the service server 130 may convert an exercise path to Geo-Hash coordinates. For example, the service server 130 may convert coordinates of an exercise path to Geo-Hash coordinates with respect to exercise paths collected during a period of time from the user starts exercise until the user finishes exercise.

In operation 1022, the service server 130 may determine whether the exercise path is included in the path database. If it is determined that the exercise path is included in the path database, the service server 130 may perform operation 1023.

In operation 1023, the service server 130 may determine whether a matching rate between the exercise path and a path included in the path database is M % or more. For example, when M=90, the service server 130 may verify whether a matching rate between the exercise path and the path included in the path database is 90% or more. Here, when the matching rate between the exercise path and the path included in the path database is M %, e.g., 90%, or more, the service server 130 may perform operation 1024.

In operation 1024, the service server 1030 may verify and issue an issuable POI badge within the exercise path.

In operation 1041, the user terminal 110 may verify the acquired POI badge and exercise path.

If the exercise path is not included in the path DB as determined in the operation 1022, or if the matching rate between the exercise path and the path included in the path database is less than M %, e.g., 90%, as determined in the operation 1023, operation 1031 may be performed.

In operation 1031, the user terminal 110 may verify the exercise path. For example, an issuable POI badge is absent in the exercise path of the user. Thus, the user may verify the exercise path through the user terminal 110. Accordingly, a process according to the illustrated embodiment may be terminated.

Although a user activity "exercise" is described as an example of illustrated embodiments using a moving path, the aforementioned description may be applicable to a case in which a movement occurs even in a user activity "daily life" or other categories of user activities.

Figure 11:
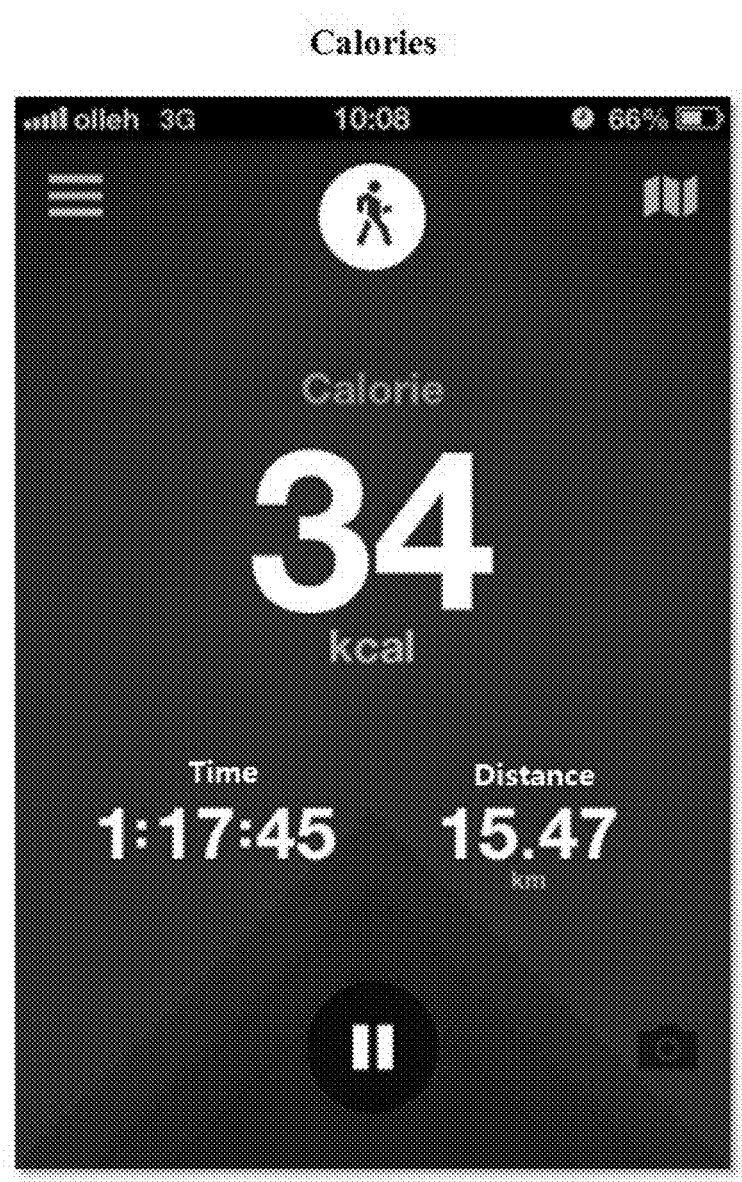
FIGS. 11 through 15 illustrate examples of a screen on which an exercise amount is displayed for each type of exercise according to an exemplary embodiment of the present invention.
Figure 12:
Figure 13:
Figure 14:
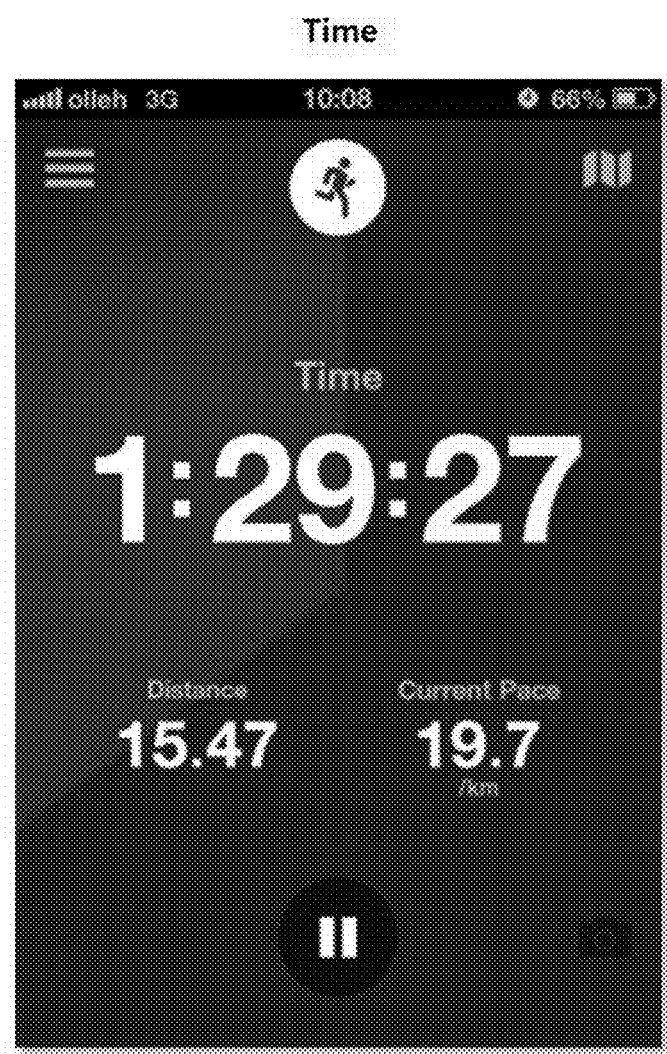
Figure 15:

FIG. 11 through FIG. 15 illustrate examples of a screen on which an exercise amount is displayed for each type of exercise according to an exemplary embodiment of the present invention. FIG. 11 illustrates a screen on which calories consumption amount is displayed, FIG. 12 illustrates a screen on which a current moving speed, for example, a current pace, is displayed, FIG. 13 illustrates a screen on which an altitude is displayed, FIG. 14 illustrates a screen on which an exercise time is displayed, and FIG. 15 illustrates a screen on which a distance is displayed.

Figure 16:
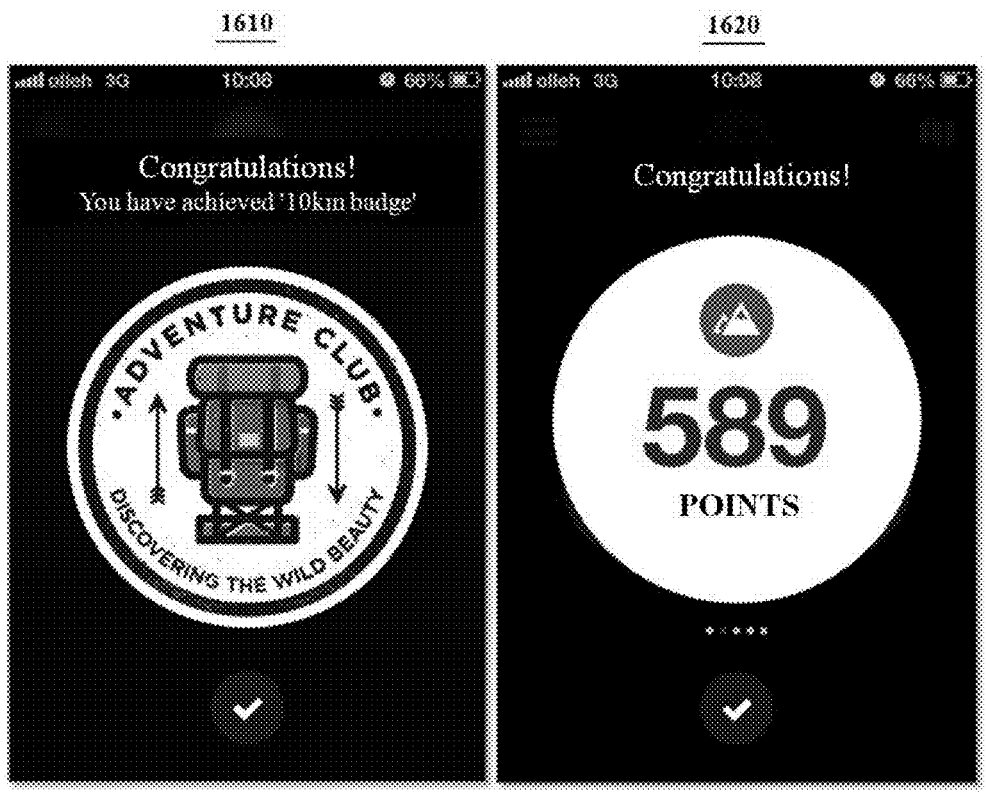
FIG. 16 illustrates an example of a screen for acquiring a badge and points according to an exemplary embodiment of the present invention.

FIG. 16 illustrates an example of a screen for acquiring a badge and points according to an exemplary embodiment of the present invention. An example in which a badge is acquired is displayed on a first screen 1610, and an example in which points are acquired is displayed on a second screen 1620.

Figure 17:
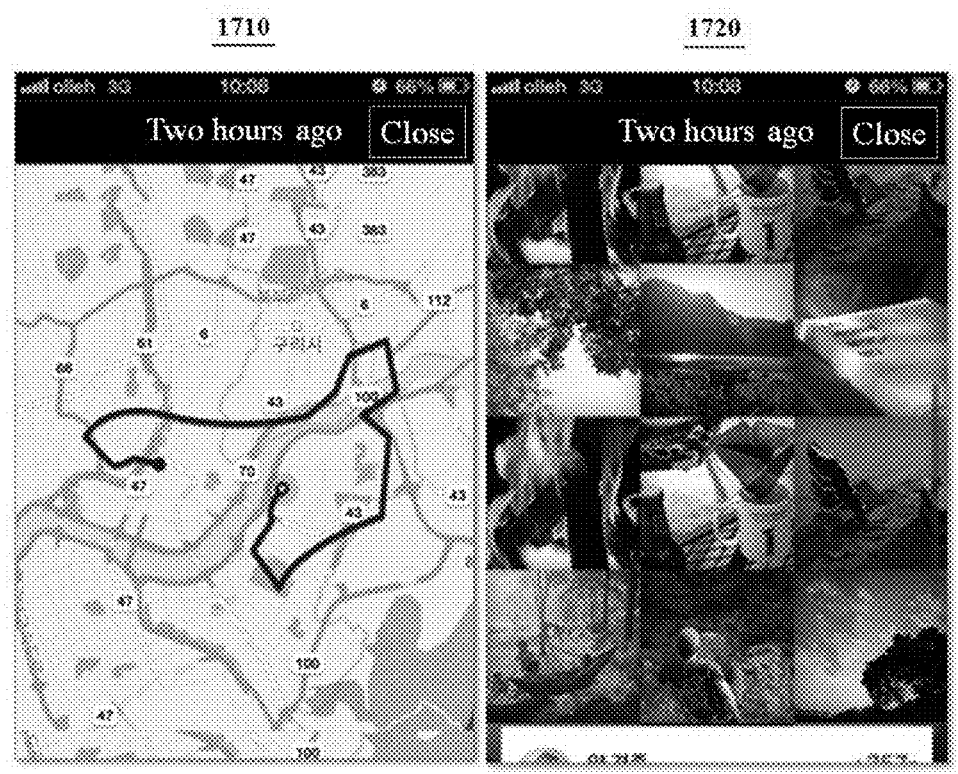
FIG. 17 illustrates an example of a screen for sharing a record according to an exemplary embodiment of the present invention.

FIG. 17 illustrates an example of a screen for sharing a record according to an exemplary embodiment of the present invention. An example of displaying and sharing a moving path of a user on a map is displayed on a first screen 1710, and an example of taking photos while moving, and uploading and sharing the photos is displayed on a second screen 1720.

Figure 18:
FIG. 18 illustrates an example of a screen on which a badge and an item book are displayed according to an exemplary embodiment of the present invention.

FIG. 18 illustrates an example of a screen on which a badge and an item book are displayed according to an exemplary embodiment of the present invention. An example of displaying various types of badges on a screen is displayed on a first screen 1810, and an example of displaying item books on a screen is displayed on a second screen 1820.

The service server may include at least one storage unit, e.g., a memory, and the like, and at least one processor, and operations performed by the service server 130 may be processed according to a control of the at least one processor.

As described above, according to illustrated embodiments, it may possible to maintain and motivate an activity of a user by measuring and recording an activity of the user including a moving path and an exercise amount as well as a location of the user, by determining a ranking of the user based on the activity of the user, and by issuing digital content as a reward for the activity of the user.

The units described herein may be implemented using hardware components, software components, or a combination thereof. For example, a processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will be appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums.

The above-described example embodiments of the present invention may be recorded in non-transitory computer-readable media including program instructions to implement various operations embodied by a computer. The media may also include, alone or in combination with the program instructions, data files, data structures, and the like. Examples of non-transitory computer-readable media include magnetic media such as hard disks, floppy disks, and magnetic tape; optical media such as CD ROM disks and DVDs; magneto-optical media such as floptical disks; and hardware devices that are specially configured to store and perform program instructions, such as read-only memory (ROM), random access memory (RAM), flash memory, and the like. Examples of program instructions include both machine code, such as produced by a compiler, and files containing higher level code that may be executed by the computer using an interpreter. The described hardware devices may be configured to act as one or more software modules in order to perform the operations of the above-described example embodiments of the present invention, or vice versa.

Although various exemplary embodiments of the present invention have been shown and described, the present invention is not limited to the described exemplary embodiments. Instead, it would be appreciated by those skilled in the art that changes may be made to the illustrated embodiments without departing from the principles and spirit of the invention, the scope of which is defined by the claims and their equivalents.

What is claimed is:

1. A service method performed by a computer configured to provide user activity monitoring services based on a plurality of activity modes of a terminal of a user, the method comprising:
   identifying, by a processor, an activity mode of the terminal of a user, the activity mode comprising a first activity mode and a second activity mode;
   in response to a determination that the activity mode of the user is the first activity mode, receiving, from the terminal of the user, activity measurement data of the first activity mode measured by an activity measurement sensor activated for the first activity mode;
   in response to a determination that the activity mode of the user is the second activity mode set by the user, receiving location information from the terminal of the user, measuring a moving path of the user based on the location information, managing target information corresponding to at least one of a type of exercise that the user is engaged in and a predetermined path, providing, by the computer, the target information to the user based on the measured moving path, receiving a response to the target information from the terminal of the user, and verifying whether the user participates in the target information based on the response; and
   generating a digital reward for the user based on the activity measurement data of the first activity mode, storing the generated digital reward in a personal profile area associated with the user, transmitting a notification message to the terminal of the user, the notification message comprising information of the generated digital reward, and providing the user with a challenge participation in a multi-user exercise of the second activity mode by processing the generated digital reward as an application fee,
   wherein the location information is acquired by a location sensor activated for the second activity mode, and
   wherein a sensor utilized in the first activity mode and a sensor utilized in the second activity mode are different.

2. The method of claim 1, further comprising:
   providing digital content corresponding to the moving path to the user in response to the verification that the user participates into the target information.

3. The method of claim 1, wherein the measuring of the moving path comprises further measuring an exercise amount about the moving path, and
   the method further comprising:
   calculating an activity amount of the user based on the moving path and the exercise amount; and
   providing additional digital content to the user based on the activity amount of the user.

4. The method of claim 1, wherein the providing of the target information to the user comprises providing the target information to the user by comparing a moving path of the user who is engaged in a type of exercise corresponding to the target information and the predetermined path.

5. The method of claim 1, further comprising:
   determining rankings of users based on exercise records of the users about the predetermined path.

6. The method of claim 5, further comprising:
   providing the user with an exercise record of another user who is ranked higher than the user; and
   providing additional digital content in response to a determination that the user achieves the exercise record of the other user.

7. The method of claim 1, further comprising:
   providing digital content corresponding to goal achievement to the user in response to a determination that the user achieves a goal set about the predetermined path.

8. The method of claim 7, wherein the set goal comprises at least one of a distance and a time set about the predetermined path, and
   wherein the user achieves the goal indicates that the user moves at least the distance along the predetermined path, passes the path within the time, or passes at least the distance within the time.

9. The method of claim 1, further comprising:
   creating a challenge comprising a goal about the path in response to a request of the user or an affiliated company; and
   providing digital content corresponding to the challenge to a user having achieved the goal of the challenge among users.

10. A non-transitory computer-readable medium storing a program, when executed by a computer, to perform the method of claim 1.

11. A service system, comprising:
    at least one memory; and
    at least one processor,
    wherein the at least one processor is configured to:
    identify an activity mode of the terminal of a user, the activity mode comprising a first activity mode and a second activity mode;
    in response to a determination that the activity mode of the user is the first activity mode, receive, from the terminal of the user, activity measurement data of the first activity mode measured by an activity measurement sensor activated for the first activity mode;
    in response to a determination that the activity mode of the user is the second activity mode set by the user, receive location information from the terminal of the user, measure a moving path of the user based on the location information, manage target information corresponding to at least one of a type of exercise that the user is engaged in and a predetermined path, provide the target information to the user based on the measured moving path, receive a response to the target information from the terminal of the user, and verify whether the user participates in the target information based on the response; and
    generate a digital reward for the user based on the activity measurement data of the first activity mode, store the generated digital reward in a personal profile area associated with the user, transmit a notification message to the terminal of the user, the notification message comprising information of the generated digital reward, and provide the user with a challenge participation in a multi-user exercise of the second activity mode by processing the generated digital reward as an application fee,
    wherein the location information is acquired by a location sensor activated for the second activity mode, and
    wherein a sensor utilized in the first activity mode and a sensor utilized in the second activity mode are different.

12. The service system of claim 11, wherein the at least one processor is configured to further process:
    a process of providing digital content corresponding to the moving path to the user in response to the verification that the user participates into the target information.

13. The service system of claim 11, wherein the at least one processor is configured to further measure an exercise amount about the moving path during the process of measuring the moving path, and is configured to further process:

a process of calculating an activity amount of the user based on the moving path and the exercise amount; and a process of providing additional digital content to the user based on the activity amount of the user.

14. The service system of claim 11, wherein during the process of providing the target information to the user, the at least one processor is configured to provide the target information to the user by comparing a moving path of the user who is engaged in a type of exercise corresponding to the target information and the predetermined path.

15. The service system of claim 11, wherein the at least one processor is configured to further process a process of determining rankings of users based on exercise records of the users about the predetermined path.

16. The service system of claim 11, wherein the at least one processor is configured to further process a process of providing digital content corresponding to goal achievement to the user in response to a determination that the user achieves a goal set about the predetermined path.

17. The service system of claim 11, wherein the at least one processor is configured to further process:

a process of creating a challenge comprising a goal about the path in response to a request of the user or an affiliated company; and a process of providing digital content corresponding to the challenge to a user having achieved the goal of the challenge among users.

18. A file distribution system for distributing a file to install an application in a terminal of a user, the file distribution system comprising:

a file storage configured to store and maintain the file; and a file transmitter configured to transmit the file to the terminal in response to a request of the user, wherein the application comprises one or more modules to perform:

controlling the terminal to display a user interface for selecting one of a daily mode and an exercise mode on a screen;

controlling the terminal to transmit activity measurement data of the daily mode measured by an activity measurement sensor activated for the daily mode;

controlling the terminal to transmit location information to a service server in response to a selection on the exercise mode;

controlling the terminal to measure an activity amount and to transmit the measured activity amount to the service server in response to a selection on the daily mode;

controlling the terminal to receive target information from the service server and to display the target information about the screen;

controlling the terminal to respond to the target information and determine whether to participate in the target information;

generating a digital reward for the user based on the activity measurement data of the first activity mode;

storing the generated digital reward in a personal profile area associated with the user;

transmitting a notification message to the terminal of the user, the notification message comprising information of the generated digital reward; and providing the user with a challenge participation in a multi-user exercise of the second activity mode by processing the generated digital reward as an application fee, wherein a sensor utilized in the daily mode and a sensor utilized in the exercise mode are different, and wherein the target information corresponds to at least one of a type of exercise that the user is engaged in and a predetermined path, and is selected based on a moving path that is measured based on the location information.

19. The service method of claim 1, wherein the first activity mode comprises a daily life mode, and the second activity mode comprises an exercise mode.

* * * * *